United States Patent [19]

Richmond

[11] 4,005,844
[45] Feb. 1, 1977

[54] SOLUTION BOTTLE HOLDER

[75] Inventor: James W. Richmond, Comstock Township, Kalamazoo County, Mich.

[73] Assignee: Stryker Corporation, Kalamazoo, Mich.

[22] Filed: Aug. 25, 1975

[21] Appl. No.: 607,202

[52] U.S. Cl. ............................. 248/311.3; 248/313; 248/318
[51] Int. Cl.² .................................... B42F 13/00
[58] Field of Search ............. 5/92; 24/31, DIG. 18; 128/214 R, 227; 222/181; 215/100 A; 248/102–106, 121, 122, 125, 313, 316 R, 318, 311.1, 311.3

[56] References Cited

UNITED STATES PATENTS

| 2,349,054 | 5/1944 | Phipps | 248/106 |
| 2,470,524 | 5/1949 | Scudder | 5/92 X |
| 2,936,992 | 5/1960 | Browning | 248/313 UX |
| 3,313,511 | 4/1967 | Koerner et al. | 24/DIG. 18 |
| 3,318,457 | 5/1967 | Krasnoff | 248/125 X |
| 3,426,363 | 2/1969 | Girard | 24/DIG. 18 |
| 3,547,322 | 12/1970 | Dawson et al. | 128/214 R X |
| 3,709,372 | 1/1973 | Alexander | 248/318 X |
| 3,797,792 | 3/1974 | Huber | 248/125 X |

Primary Examiner—Lawrence J. Staab
Attorney, Agent, or Firm—Woodhams, Blanchard and Flynn

[57] ABSTRACT

An elongated relatively rigid member is removably attached by securing means to a side element of a wheeled patient carrier, such as a stretcher, so that said elongated member is in a relatively upright position. Hanger means are provided at the top of the elongated member for supporting engagement with the hanger bail of a bottle for suspending the bottle in an inverted position so that its contents can be delivered, as through a tube, to a patient on a stretcher. A clamp means is adjustably secured to the elongated member, and strap means is fixedly connected at one end to said clamp member and releasably connected at its outer end to said clamp member for surrounding and firmly holding the bottle against said clamp member.

5 Claims, 3 Drawing Figures

SOLUTION BOTTLE HOLDER

BACKGROUND OF THE INVENTION

This invention relates in general to an apparatus for supporting a bottle containing a solution being delivered to a patient on a wheeled carrier, and, more particularly, to a type of such apparatus which is capable of preventing damage to the bottle from swinging or dropping or falling when the patient is being transported on the wheeled carrier.

For many years, persons, such as medical doctors and nurses, have been aware of the importance of maintaining a continuous, regulated flow of solutions being delivered to a patient particularly following serious surgery, a serious accident or both. In the past, it has been at least acceptable practice to shift the patient from an operating table to a patient transport, such as a wheeled stretcher, for the transporting of the patient to an intensive care unit or to a recovery room. Frequently, solutions of one or more type must be delivered to the patient during the period immediately following the surgery or admission to the Emergency Room of the hospital and it is especially important that such delivery of the solution not be interrupted even for a relatively short period of time. Heretofore, it has been common practice for an orderly or technician to hold the solution bottle and manually carry it during the transport of a patient. Where the person holding the bottle must also be assisting in the transport of the patient, the bottles are sometimes dropped or lowered to a position where the flow by gravity is interrupted, or the bottle is bumped against a door jamb or the like and broken. Obviously, any one of these three eventualities results in an interruption of the flow of solution to the patient.

In some instances, the solution bottles are loosely suspended from a support attached to the wheeled transport but they are allowed to freely swing and, as a result, are often broken. In extreme cases of movement, as where being handled manually, such movement of the bottles can result in disconnection thereof from the patient, even though the bottle remains intact.

It follows from the foregoing, therefore, that there has been a serious need for a structure which will positively but quickly releasably hold a solution bottle in a fixed and protected position relative to the patient being transported upon a wheeled carrier. Accordingly, a primary object of this invention has been the provision of an apparatus for firmly, but quickly removably, holding a solution bottle in a fixed position relative to a rigid support on a wheeled carrier and patient being transported by the carrier.

Other objects and purposes of the invention will become apparent to persons familiar with this type of apparatus upon reading the following specification and examining the accompanying drawings, in which.

Figure 1:
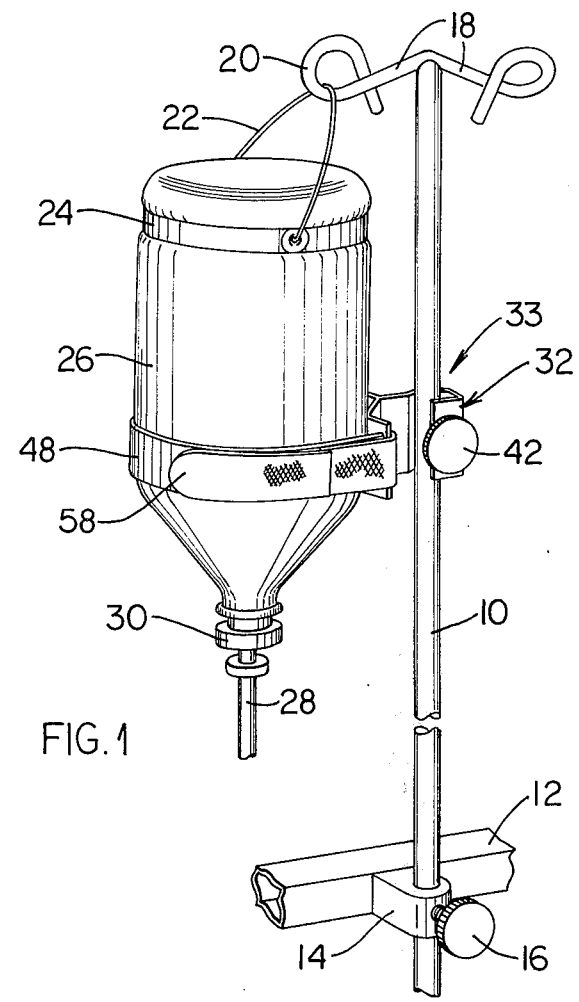
FIG. 1 is a fragmentary prospective view showing a solution bottle mounted on the support of the invention which is attached to a portion of a stretcher.

For convenience in description the terms "up", "down" and words of similar import will have reference to the apparatus of the invention as appearing in FIG. 1. The terms "in", "out" and derivatives thereof will have reference to the geometric center of said apparatus and parts thereof.

SUMMARY OF THE INVENTION

The invention lies in the provision of a bottle holder including a clamp having a first adjustable connection which may be moved vertically along an upright support to adjust to solution bottles of different lengths, and a second adjustable connection to releasably retain bottles of different diameter to the vertically adjusted position of the body of the clamp.

DETAILED DESCRIPTION

As shown in FIG. 1, a preferred embodiment of the invention comprises a rigid, upright rod 10 which is connected to the side rail 12 or other rigid part of a hospital stretcher or bed by extending through a vertical opening in a projection on the side rail, where said rod is vertically adjustably held by a set screw having a hand knob 16. The support rod has oppositely extending hanger arms 18 on its top, and the ends of the arms are twisted spirally into hooks 20. The hooks supportingly engage the bail 22 attached to the hanger band 24 which extends around the upper (closed) end of a solution bottle 26 when the bottle is inverted. A flexible delivery tube 28 is connected to the neck of the bottle by a suitable connecting plug or cork 30. The bottle is a piece of familiar hospital equipment, and means for supporting it in an inverted position are also well known.

Figure 2:
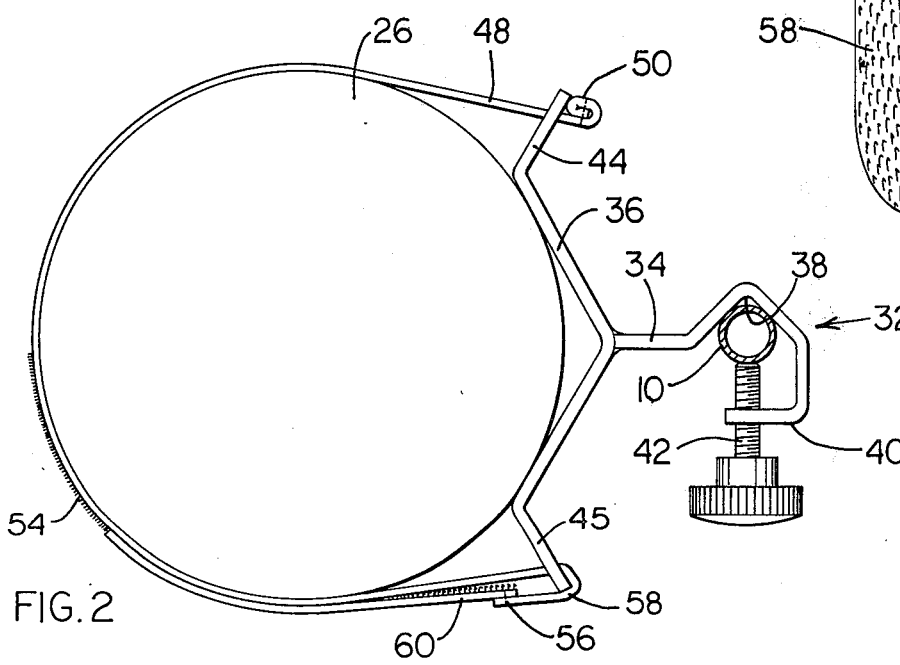
FIG. 2 is a horizontal cross sectional view through the elongated upright support on the stretcher, showing the clamp in clamping relation to the bottle.

The bracket 32 of the clamp 33 consists of a first rigid arm 34 (FIG. 2) projecting laterally from the middle of a cross bar 36. The arm 34 and bar 36 are generally co-planar and horizontal in use. The arm 34 has a V-shaped saddle or seat 38 formed therein to receive a section of the upright rod 10, and the end of the arm is reversely bent so that it has an end portion 40 arranged to receive the set screw 42. The screw engages the rod 10 and forces it into the saddle 38 and permits the bracket to be clamped to the rod at any selected elevation.

The cross bar 36 is laterally concave away from the arm 34 to form a second seat engageable with the sides of bottles 26 of differing diameters. Ears 44 and 45 on the ends of the cross bar are bent away from the bottle and they have elongated slots 46 and 47, respectively, formed therethrough.

Figure 3:
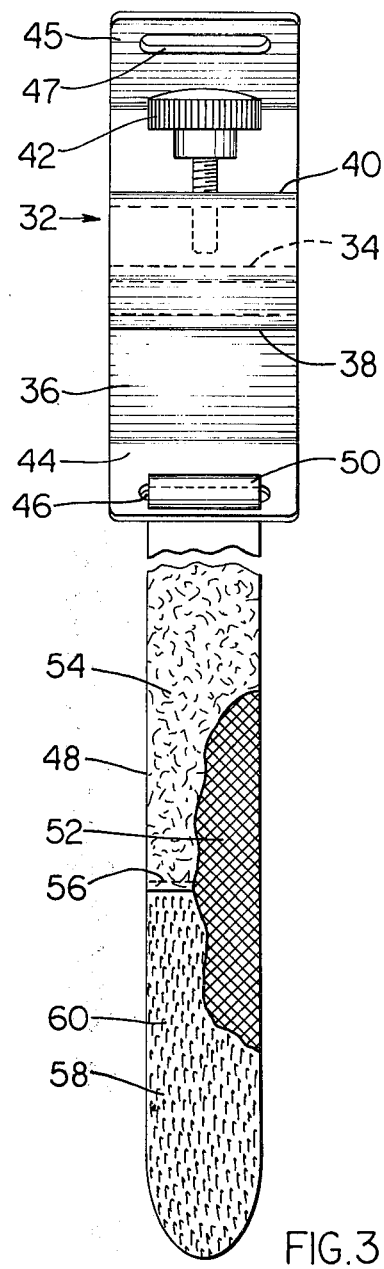
FIG. 3 is a broken plan view of the clamp in flat, extended position.

A flexible strap 48 (FIG. 2) extends through the slot 46, and has one end portion folded upon itself and stitched to form a knob 50 at the end of the strap which knob cannot pass through the slot. The strap 48 (FIG. 3) desirably has a woven fabric backing on one side, as at 52, and the opposite side is provided with thick fibers, as at 54 in FIG. 2, which fibers are loose at one end. Secured to the end of the strap 48, as by stitching at 56 and remote from the knob 50, is a strip 58 which has a multiplicity of flexible plastic hook elements 60 on the same side of the strap as the fibers 54. The loose fibrous portion 54 and the strip 58 with the flexible hooks form a readily releasable and selectively connectible connection which is identifiable as a commercially available item under the tradename VELCRO.

OPERATION

After the solution bottle is hung on the hook 20, the bracket 32 is adjusted vertically along the rod 10 to the side of the bottle 26. The strap 48 is then wrapped around the bottle with the loose fiber side on the outside. The end strip 58 is pulled through the slot 47 in the ear 45 of the bracket and folded back onto the fibrous surface so the plastic hook elements 60 engage the fibers 54. The bottle is thus held against swinging and accidental disengagement from the hook 20.

Although a particular, preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. An apparatus removably attachable to a wheeled patient carrier for supporting on said carrier a bottle of solution being delivered to a patient, the bottle having a suspending element associated therein for permitting it to be suspended in an inverted position, the combination comprising:

an elongated rigid rodlike support member;

means releasably attaching said support member to the carrier in an upright position wherein said support member projects upwardly from the carrier;

hanger means fixed on the upper end of said elongated member and engageable with said suspending element for suspending said bottle in an inverted position;

bracket means releasably secured to said elongated support member at a location spaced downwardly from said hanger means and being adjustable lengthwise of said support member, said bracket means including an angled bar having two flat plate-like parts which extend at an angle relative to one another and define a shallow V-shaped recess for receiving said bottle;

flexible strap means connected at one end to said bar adjacent an outer edge of one of said flat parts, said strap means being extendible around said bottle and connectible with said bar adjacent an outer edge of the other flat part whereby said bottle is held firmly within said V-shaped recess against said bar, said strap means being flat and having two sections connected end-to-end, said sections having coacting and interengageable fastening means on the same sides thereof; and said bracket means having a slot in one end of said bar whereby said strap means may be passed through said slot and folded back onto itself to adjustably selectively engage said fastening means at various positions to maintain said bottle snugly against said bar.

2. An apparatus according to claim 1, wherein said bracket means includes a hook-shaped arm fixed to said bar and projecting rearwardly therefrom, said hook-shaped arm having one end thereof fixed to said bar substantially at the intersection between said flat parts, said hook-shaped arm having an open hook portion which includes a V-shaped part defining therein a V-shaped aperture in which is received said support member, said support member being of circular cross-section, and said hook portion having a mounting part which is spaced opposite said V-shaped part so that the support member is disposed therebetween, and said bracket means including a threaded locking element supported on said mounting part and engageable with said support member for fixedly but releasably securing said bracket means to said support member.

3. An apparatus according to claim 2, wherein said angled bar includes a pair of flanges which are fixed to the outer edges of said flat parts and project rearwardly therefrom so that said angled bar thus has a substantially W-shaped configuration, one of said flanges having said slot formed therein, and said strap means after it extends around said bottle having the opposite ends thereof connected to said flanges.

4. An apparatus according to claim 2, wherein said fastening means includes a fibrous surface on one section of the strap means and a multiplicity of plastic hook elements on the other section of the strap means.

5. An apparatus according to claim 1, wherein said fastening means includes a fibrous surface on one section of the strap means and a multiplicity of plastic hook elements on the other section of the strap means.

* * * * *